United States Patent
Zuo (10) Patent No.: US 11,278,734 B2
(45) Date of Patent: Mar. 22, 2022

(54) SYSTEMS AND METHODS FOR NAIL TREATMENT

(71) Applicant: BLOSSOM INNOVATIONS, LLC, Waltham, MA (US)

(72) Inventor: Vincent Zuo, Boston, MA (US)

(73) Assignee: BLOSSOM INNOVATIONS, LLC, Waltham, MA (US)

( * ) Notice: Subject to any disclaimer, the term of this patent is extended or adjusted under 35 U.S.C. 154(b) by 0 days.

(21) Appl. No.: 16/838,172

(22) Filed: Apr. 2, 2020

(65) Prior Publication Data

US 2020/0368548 A1 Nov. 26, 2020

Related U.S. Application Data

(60) Provisional application No. 62/828,086, filed on Apr. 2, 2019.

(51) Int. Cl.
*A61N 5/06* (2006.01)
*A61N 5/067* (2006.01)

(52) U.S. Cl.
CPC ............ *A61N 5/0613* (2013.01); *A61N 5/067* (2021.08); *A61N 2005/0628* (2013.01); *A61N 2005/0651* (2013.01); *A61N 2005/0654* (2013.01); *A61N 2005/0659* (2013.01); *A61N 2005/0663* (2013.01); *A61N 2005/0667* (2013.01)

(58) Field of Classification Search
CPC .......... A61N 5/0613; A61N 2005/0642; A61N 2005/0651; A61N 2005/0654; A61N 5/06; A61N 2005/0628
See application file for complete search history.

(56) References Cited

U.S. PATENT DOCUMENTS

| 2006/0004425 A1* | 1/2006 | Cumbie | ............... A61L 2/10 |
| | | | 607/86 |
| 2009/0012515 A1* | 1/2009 | Hoenig | ............... A61B 18/203 |
| | | | 606/33 |
| 2010/0234925 A1* | 9/2010 | Harris | ............... A61N 5/0616 |
| | | | 607/88 |

OTHER PUBLICATIONS

MSP430FR2633 Capacitive Touch MCU with 16 touch I) (64 sensors), 16KB FRAM, 4KB SRAM, 19 IO, 10-bit. ADC [From the Internet] http://www.ti.com/product/MSP430FR2633.
High Power color LEDs in a micro footprint package for ultimate design flexibility [From the Internet] https://www.luxeonstar.com/assets/downloads/ds105.pdf, 2017.

(Continued)

*Primary Examiner* — Carl H Layno
*Assistant Examiner* — Aya Ziad Bakkar
(74) *Attorney, Agent, or Firm* — Hunton Andrews Kurth LLP (57) ABSTRACT

Exemplary system and method are provided for affecting nail growth rate, which can use a light dosage and a wavelength of light to affect a growth rate of a nail of a subject. For example, it is possible to detect a presence of a nail using, e.g., a presence detector. The nail can be irradiated over a treatment time with a light having a wavelength and a power, e.g., using a narrowband light source. Further, using a controller, it is possible to control one or more of the power and the treatment time to irradiate the nail with a light dosage that is within a biphasic light dosage range bounded by a lesser light dosage and a greater light dosage. The wavelength of the light and the light dosage can be configured to affect a growth rate of the nail.

30 Claims, 9 Drawing Sheets

(56) References Cited

OTHER PUBLICATIONS

High power infrared emitters enabling the next level of design flexibility [From the Internet] https://www.luxeonstar.com/assets/downloads/ds190.pdf.
Orentreich et al., "The Effect of Aging on the Rate of Linear Nail Growth" The Journal of Investigative Dermatology, 73:126-130, 1979.
Westerberg et al., "Onychomycosis: Current trends in diagnosis and treatment" American Family Physician, vol. 88, No. 11, Dec. 2013.
Karu et al., "Exact Action Spectra for Cellular Responses Relevant to Phototherapy" Photomedicine and Laser Surgery, vol. 23, No. 4, pp. 355-361, 2005.
Zein et al., "Review of Light Parameters and Photobiomodulation Efficacy: Dive into Complexity" Journal of Biomedical Optics, 23(12), 120901, Dec. 2018.
Huang et al., "Biphasic Dose Response in Low Level Light Therapy" Dose-Response 7, p. 358-383, 2009.
International Preliminary Report on Patentability for International Patent Application No. PCT/US2020/026325 dated Oct. 14, 2021.

\* cited by examiner

SYSTEMS AND METHODS FOR NAIL TREATMENT

CROSS-REFERENCE TO RELATED APPLICATION(S)

This application relates to and claims priority from U.S. Patent Application Ser. No. 62/828,086, filed on Apr. 2, 2019, the entire disclosure of which is incorporated herein by reference.

FIELD OF THE DISCLOSURE

The present disclosure relates to exemplary systems and methods for effectuating a treatment of a portion of a body (e.g., a nail), and more particularly, to exemplary systems and methods for providing a photo-biomodulation of fingernails and toenails.

BACKGROUND INFORMATION

Nails support and protect the sensitive tips of our fingers and toes. Fingernails can also assist with picking up objects. Fingernails and toenails can further be used as indicator(s) of a systemic health over time. It is not uncommon for a doctor performing a checkup to initially check patient's fingernails to seek indications of previous stress or illness in the nails of the patient. Fingernails and toenails are also prominently located on exposed digits. It is thus understood that healthy looking fingernails and toenails are aesthetically appealing and sought after by many, e.g., in nail salons.

Nail salons have services which polish, color, gel-coat, and adhere false nails to make fingernails and toenails appear longer and healthier. However, many of these efforts to make nails appear healthier are deleterious to nail health. Nail polish and coatings must be removed as the nail grows. Removal of nail polish requires the use of solvents, such as acetone; and, removal of gel-coating can require solvents as well as elevated temperatures. The polish or coating once removed often reveals a thinner, more brittle, and discolored nail.

Additionally, broken and scratched nails can often frustrate the appearance of long and healthy nails and it becomes necessary to wait for such problematic nails to regrow. A faster growing fingernail or toenail therefore is more likely to appear healthy, as it will regrow faster after a break and replenish sooner after discoloration and thinning from damaging nail cosmetics.

Figure 1:
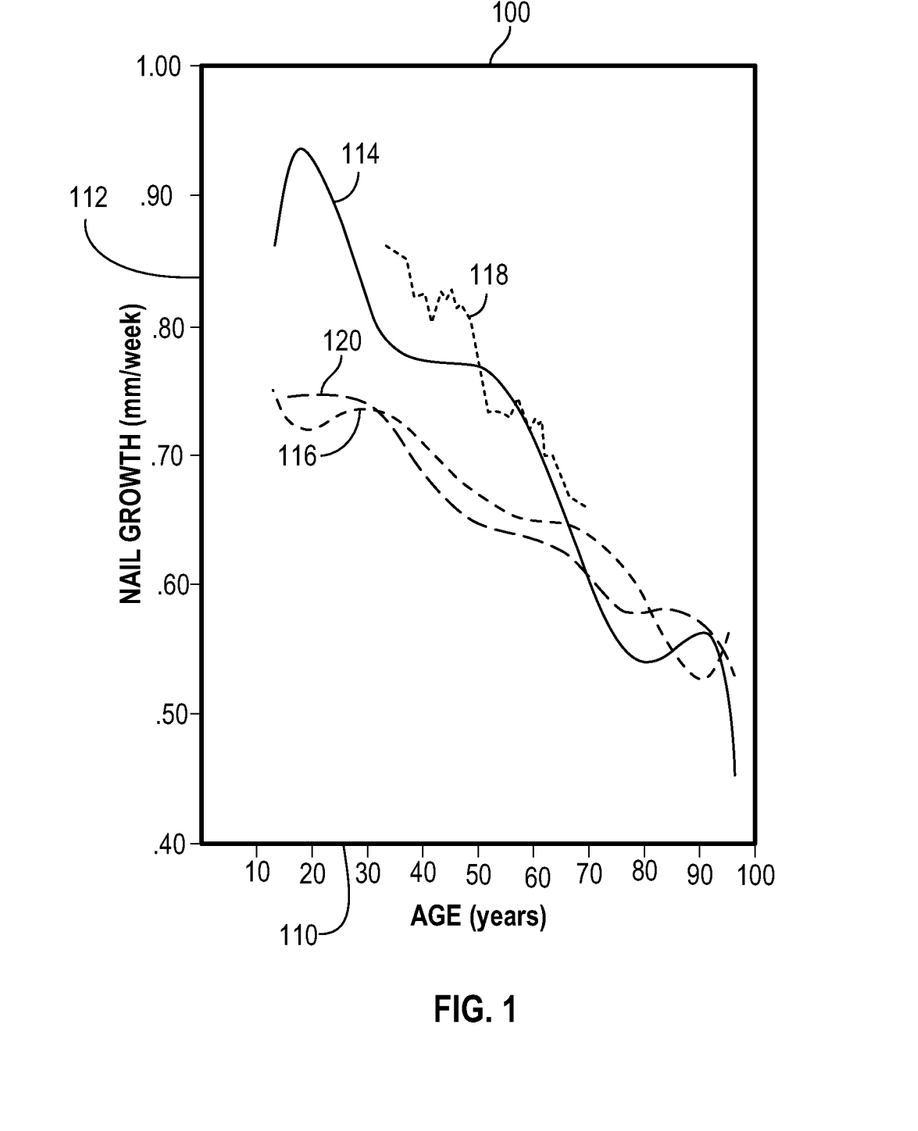
FIG. 1 is a graph showing nail growth rate as a function of age as reported by several prior studies.

Nail growth rate is known to decrease with age. FIG. 1 illustrates a graph 100 that shows age in years along a horizontal axis 110 and human linear nail growth rate in millimeters per week along a vertical axis 112. This graph of FIG. 1 provides exemplary results from 4 separate long-term cross-sectional and longitudinal studies. A curve 114 indicates the results for a first study which was cross-sectional and included 72 participants. A curve 116 indicates the results for a second study which was also cross-sectional and included 185 participants. A curve 118 indicates the results for a third study which was a longitudinal study over years 32 to 68. And finally, a curve 120 indicates the results for a forth study which was cross-sectional and included 1056 participants. Additional information on these studies can be found in "The Effect of Aging on the Rate of Linear Nail Growth" by Orentreich, Markofsky and Vogelman, published in The Journal of Investigative Dermatology 1979, and incorporated herein by reference in its entirety. Indeed, the graphs and curves 114, 116, 118 and 120 of FIG. 1 indicate an apparent trend that nail growth slows with age.

Faster growing nails can result in aged, scratched, damaged, or broken nails being replaced with fresh undamaged nails in less time. This can be advantageous, e.g., for those desiring healthier looking nails, as well as for many others. For example, string musicians (e.g., guitarists) often require thick, strong and long nails to pluck the strings of their respective instruments. This ability can be significantly degraded after a fingernail is broken and before it grows back. Additionally, those suffering from certain nail diseases may not be fully cured of the disease until all of the infected nail has grown out and been trimmed away. A patient with the nail disease may often require treatment to continue for as long as the diseased nail is still present and/or not cured.

For the aforementioned reasons as well as for reasons not mentioned, it would be beneficial to address the above-described deficiencies, including, e.g., to provide a safe, effective, at-home treatment that can affect a nail growth rate.

SUMMARY OF EXEMPLARY EMBODIMENTS

To that end, devices, systems and methods can be provided to address at least some of the deficiencies described herein above. Such exemplary systems, devices and methods can be used by medical, veterinary and aesthetics professionals, as well as ordinary individuals (e.g., non-clinician or user) to effectively alter the nail growth rate without risk of serious side effects. The exemplary systems, devices and methods can be utilized in a variety of settings including, but not limited to, clinical, spa and/or at home settings. As described herein above, various reasons exist for altering individual's nail growth rate. An example of one such reason can be to treat nail disease.

In certain exemplary embodiments of the present disclosure, an increase in nail growth rate can be used as a treatment for diseased nails. Onychomycosis (i.e., tinea unguium) is a fungal infection of the nail, whereas toenails and fingernails may be affected. However, toenails are more often to be affected by onychomycosis. Symptoms of onychomycosis include nail discoloration, thickening of the nail, and separation of the nail from the nail bed. Onychomycosis is usually caused by a fungal infection. Infecting mycosis commonly include species of the genera: *Candida, Fusarium, Microsporum, Epidermophyton*, and *Trichophyton*.

Current onychomycosis treatments can include, e.g., systemic antifungal medication, topical antifungal medication, and exemplary laser treatments. Exemplary laser treatments for Onychomycosis utilize a laser to heat an infected nail bed to a high temperature (e.g., about 40-60° C.), at this temperature fungal mycelium is damaged or destroyed, however fungal spores are unaffected. As a patient with onychomycosis may have many spores within and under the nail plate, reinfection can often occur. Information regarding possible diagnosis and treatments of onychomycosis is available in "Onychomycosis: Current trends in diagnosis and treatment" by Westerberg and Voyack, published in American Family Physician, December 2013 and incorporated herein by reference in its entirety. According to an analysis presented in such publication, systemic antifungals are currently believed to be the most effective treatment with mycotic cure rates of 76% for terbinafine, 59%-63% for itraconazole depending on dosing (e.g., pulsed or continuous), and 48% for fluconazole. As the fungal infections that cause onychomycosis typically occur under the nail plate and out of reach of a topical agent, the results in the Westerberg and Voyack publication show that the most common topical antifungal treatment, ciclopirox, has a failure rate greater than about 60%. Unfortunately, the known effective current treatments, one of which is systemic antifungal (e.g., oral tribinafine), are likely to cause serious side effects including liver damage. Additionally, topical and laser treatments that are less likely to cause side effects are less effective in treating onychomycosis. Many individuals with onychomycosis find the treatment worse than the decease, and elect not to perform any treatment. An onychomycosis treatment can therefore reduce, and likely eliminate the fungal infection without an increased risk of serious side effects.

Fungal infections causing Onychomycosis can often be caused by fungus that infect the nail via the hyponychium (i.e., the area of epithelium underlying the free edge of the nail plate). From that point, the fungus likely invades the undersurface of the nail plate, then spreading proximally toward the nail matrix. A fungus most associated with onychomycosis is *Trichophyton rubrum*. *T. rubrum* is saprotrophic and colonizes upper layers of dead skin. *T rubrum* is known to cause tinea pedis (i.e., Athlete's foot), tinea manuum, tinea cruris, and onychomycosis. Nail invasion by *T. rubrum* is likely initiated at the outermost hyponychium, and spreads inward. *T. rubrum* and other fungus typically effect the formation of white plaques on the lunula that can spread to the entire nail. Ultimately, the nail often becomes thick, brittle, and discolors.

Onychomycosis is increasingly common with age. The publication by Westerberg and Voyack states that Onychomycosis occurs in 10% of the general population, 20% of persons over the age of 60 years, and 50% of persons over the age of 70. As described in detail herein above, nail growth rate likely decreases dramatically with age as occurrences of onychomycosis increases.

Onychomycosis treatments are often frustrated or made less effective by the presence of fungal spores. As described herein above in reference to laser treatment, some fungal treatments are capable of only killing the mycelium of the fungus. Spores that remain following treatment can recolonize. Vital spores may often remain in the nail plate and are not be removed until the nail is trimmed. Nail growth rate can therefore be dependent on how long the fungus remains to potentially re-infect the nail.

Additionally, initial fungal infection of the nail can be affected by nail growth rate. As the fungal infection spreads inward from immediately under the tip of the nail toward the nail bed and the nail matrix, the nail plate grows outward toward the tip. Replenishment of the nail plate generally retards the advancing colonization of the fungus, similar to, e.g., an opposing tide in the ocean slows the progress of a boat. For this reason, a nail treatment that increases nail growth rate in older patients and those suffering from fungal infections is beneficial and performed using the exemplary embodiments of the present disclosure.

Motivations for altering (e.g., increasing or decreasing) nail growth rate and/or rate have been described in detail herein above. The exemplary embodiments according to the present disclosure provide various systems, devices and methods for affecting nail growth rate of a subject irrespective of motivation for doing so.

According to an exemplary embodiment of the present disclosure, an exemplary method can be provided for affecting nail growth rate. For example, it is possible to detect a presence of a nail of the subject using, e.g., a presence detector. The nail can be irradiated over a treatment time with a light having a wavelength and a power, e.g., using a narrowband light source. Further, using a controller, it is possible to control one or more of the power and the treatment time to irradiate the nail with a light dosage that is within a biphasic light dosage range bounded by a lesser light dosage and a greater light dosage. The wavelength of the light and the light dosage can be configured to affect a growth rate of the nail. Further, it is possible to document or record (e.g., to a computer file) and/or analyze at least one parameter related to the light dosage, e.g., possibly using the controller and/or a computer device.

According to another exemplary embodiments of the present disclosure, a system can be provided for affecting the nail growth rate of the subject. Such exemplary system can comprise a presence detector, a narrowband light source, and a controller. The presence detector can be configured to detect a presence of the nail. The narrowband light source can be configured to irradiate the nail over a treatment time with a light. The controller can be configured to control the power of the light and/or the treatment time to irradiate the nail with a light dosage that is within a biphasic dosage range bounded by a lesser dosage and a greater dosage. The controller (or another computer device) can be configured to document (or record) and/or analyze at least one parameter related to the light dosage, which can be to a log file or into any other format or file. The wavelength of the light and the light dosage can be configured to affect a growth rate of the nail.

In still further exemplary embodiments of the present disclosure, it is possible to determine and/or estimate a treatment irradiance based upon the presence of the nail of the subject at a known location and the power of the light, and/or the light dosage based upon the treatment irradiance.

Some other exemplary embodiments of the present disclosure, it is possible to use a photodiode to measure a treatment irradiance; and, controlling the light dosage based upon the treatment irradiance.

According to yet further exemplary embodiments of the present disclosure, the narrowband light source can be or include a light emitting diode, a light emitting capacitor, a laser, a flash lamp, and/or a filtered wideband light source.

Some exemplary embodiments of the present disclosure are configured to cause the nail growth rate of the subject to increase, and while other exemplary embodiments are configured to cause the nail growth rate of the subject to decrease.

According to further exemplary embodiments of the present disclosure, the parameter related to the light dosage can comprise a start time of treatment, an end time of treatment, the power of, the treatment time, and/or the light dosage. In further exemplary embodiments of the present disclosure, it is possible to verify a dosage compliance using the computer file and/or using the parameter. It is also possible to control the light dosage based upon a dosing schedule.

In additional exemplary embodiments of the present disclosure, the presence detector can comprise a pressure sensor, a camera, a time of flight (TOF) system, a LiDAR system, a capacitive proximity sensor, a photoelectric sensor, an optical sensor, an infrared sensors, and/or a switch.

In some exemplary embodiments of the present disclosure, the wavelength of the light can be 658 nm, 665 nm, 765 nm, 850 nm, and/or 855 nm. In some further exemplary embodiments of the present disclosure, the lesser light dosage can be about 0.5 J/cm' and the greater light dosage can be about 100 Fern'. In further exemplary embodiments of the present disclosure, the treatment time is within a range of 60 to 14400 seconds.

In some embodiments of the system, the controller can be further configured to estimate a treatment irradiance based upon the presence of the nail of the subject at a known location and the power of the light and control the light dosage based upon the treatment irradiance.

According to further exemplary embodiments of the present disclosure, a photodetector can be provided that is configured to measure a treatment irradiance; and, the controller is further configured to control the light dosage based upon the treatment irradiance.

In additional exemplary embodiments of the present disclosure, the narrowband light source can comprise a light emitting diode, a light emitting capacitor, a flash lamp, and/or a filtered wideband light source.

Various exemplary embodiments of the present disclosure are configured to increase the growth rate of the nail of the subject, while other exemplary embodiments of the present disclosure are configured to decrease the growth rate of the nail of the subject.

In some exemplary embodiments of the present disclosure, the one or more parameters related to the light dosage can include a start time of treatment, an end time of treatment, the treatment time, the power of the light, and/or the light dosage. For example, the controller can be configured to verify dosage compliance, e.g., using the log file, the parameter and/or any other data. According to still other exemplary embodiments of the present disclosure, the controller is configured to control the light dosage based upon a dosing schedule.

According to some additional exemplary embodiments of the present disclosure, the presence detector can include a pressure sensor, a camera, a time of flight (TOF) system, a LiDAR system, a capacitive proximity sensor, a photoelectric sensor, an optical sensor, an infrared sensors, and/or a switch.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

Exemplary Definitions

Unless otherwise defined, all technical and scientific terms used herein have the same meaning as commonly understood by one of ordinary skill in the art to which this disclosure belongs. In case of any conflict, the exemplary definitions provided in the present disclosure, as applicable, would be controlling.

A "subject" is a vertebrate, including any member of the class mammalia, including humans, domestic and farm animals, and zoo, sports or pet animals, such as mouse, rabbit, pig, sheep, goat, cattle and higher primates. It will be appreciated that a "subject" may also be referred to as a patient.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

The exemplary ranges described herein are understood to be shorthand for all of the values within the range. For example, and in no way limiting, an exemplary range of 1 to 50 is understood to include any number, combination of numbers, or sub-range from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as any fractions thereof unless the context clearly dictates otherwise).

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

In the present disclosure, the terms "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Other definitions appear in context throughout the present disclosure.

Exemplary Embodiments of Present Disclosure

Figure 2A:
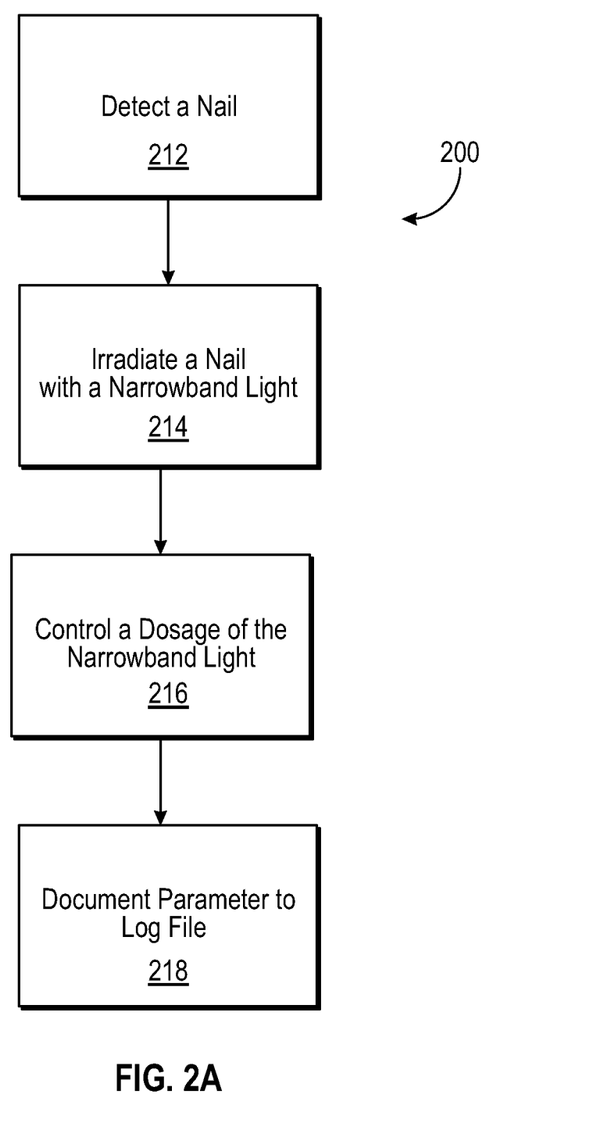
FIG. 2A is a flow diagram of a method for affecting nail growth, in accordance with an exemplary embodiment of the present disclosure.

FIG. 2A shows a flow diagram of a method 200 for a treatment of a nail to increase nail growth rate according to an exemplary embodiment of the present disclosure. As shown in FIG. 2A, a nail is detected in procedure 212. According to certain exemplary embodiments of the present disclosure, a nail can be detected by detecting the digit or limb on which the nail is provided on. In some exemplary versions and/or variants, the detection of the nail 212 can be performed by, e.g., a proximity detection and/or a pressure detection. The detection of the nail in procedure 212 can facilitate the total amount of light energy delivered to the nail (i.e., dosage) to be estimated. Without nail detection provided in procedure 212, treatment can be effectuated with the nail at an incorrect location. In this exemplary case, the amount of energy delivered to the nail may be uncertain. According to certain exemplary embodiments of the present disclosure, the detection of the nail provided in procedure 212 can also include detecting a location of the nail. For example, a presence of a nail can be detected in procedure 212 only when, e.g., a nail is positioned in a known and/or predetermined location. In certain exemplary modifications and/or versions, the known and/or predetermined location of the nail can be used to estimate treatment parameters.

Once the nail is detected, the nail can be irradiated with a narrowband light 214. In one exemplary embodiment, narrowband light can be approximated as representing only a single center wavelength. In practice, narrowband light can include mostly (e.g., greater than 50%, greater than 75%, or greater than 90%) light from a narrow wavelength band (e.g., less than lnm, less than 10 nm, less than 100 nm, or less than 500 nm).

Certain wavelengths stimulate DNA and RNA synthesis, as discussed in Karu and Kolyakov's 2005 document entitled "Exact Action Spectra for Cellular Responses Relevant to Phototherapy" published in Photomedicine and Laser Surgery and incorporated herein by reference in its entirety. The Karu and Kolyakov document indicates that light having center wavelengths of approximately 660 nm and 850 nm correspond to critical active regions for stimulated RNA and DNA synthesis. This indication can be supported in the use and success of photobiomodulation and phototherapy at these wavelengths. Examples of effective photobiomodulation are provided in Zein, Selting and Hamblin 2018 review entitled "Review of Light Parameters and Photobiomodulation Efficacy: Dive into Complexity" published in the Journal of Biomedical Optics and incorporated herein by reference in its entirety. For example, wounds, ulcers, and bone were found to be effectively treated with photobiomodulation by narrowband light centered at wavelengths including: 830 nm, 670 nm, 632 nm, and 670 nm.

A dosage of the narrowband light can be controlled in procedure 216 in order to affect (e.g., increase) a growth rate of the nail. According to certain exemplary embodiments of the present disclosure, the light dosage can be controlled by modulating an optical power of the narrowband light. For example, in some exemplary variants and/or versions, pulse width modulation (PWM) can be used to control optical power of a narrow band light source (e.g., a light emitting diode [LED]). In certain exemplary variants and/or versions, the control of the dosage in procedure 216 can be a closed loop and the optical power of the narrowband light can be actively measured, for example, using a photodetector. Examples of photodetectors can include, e.g., photodiodes, photoresistors, phototransistors, active-pixel sensors (e.g., a charge coupled device [CCD] and a capacity metal-oxide semiconductor [CMOS] sensors), and/or photovoltaic cells. In other exemplary variants and/or versions, the control of the dosage in procedure 216 can be an open loop. In this exemplary case, it can be advantageous for the control in procedure 216 be calibrated based upon a representative measured optical power of the narrowband light at the known nail location prior to treatment. Controlling power of the narrowband light can control a treatment irradiance (for example, measured in $W/cm^2$). The treatment irradiance can be the irradiance of the narrowband light as applied to the nail.

According to particular exemplary embodiments of the present disclosure, the dosage can be controlled in procedure 216 by controlling a treatment time over which the nail undergoes irradiation. The dosage can be measured according total energy delivered over total treated area or using an accumulated fluence (e.g., the treatment irradiance integrated over the treatment time). The accumulated fluence can be measured in Fern'. Controlling the treatment time, therefore, controls the light dosage as measured by accumulated fluence.

While it is certainly beneficial to alter a nail growth rate and the scientific research indicates the promise of photobiomodulation, it is believed that no commercial systems are available. Effective photobiomodulation of the nail matrix stimulates and increases nail growth, increasing a rate of growth of aged, diseased, or normal nails. The effectiveness of photobiomodulation of nails can be largely dependent on light dosage. The light dosage can determine whether the growth rate of a nail is stimulated or inhibited. Additionally, as discussed herein below, a proper light dosage during photobiomodulation has proven difficult in a research setting in the past.

In order to better control light dosing over time, according to certain exemplary embodiments of the present disclosure, it is possible to track (i.e., log or record) the use and/or light dosage over a period of time. It is understood that compliance of a subject to a treatment regimen can be an issue in many areas of healthcare, veterinary medicine and aesthetics. For example, subjects responsible for treating themselves outside of a clinical or spa setting commonly may fail to adhere to treatment regimens, thereby possibly limiting the potential effects of treatment. As effects from photobiomodulation may be very sensitive to light dosage amount (as described in detail below), a negative impact from non-compliance by a subject user of a device intended to affect nail growth rate can counteract any (and possibly all) of the desired results. In order to ensure a careful delivery of therapeutic or cosmetic light dosage, in some exemplary embodiments of the present disclosure, one or more parameters can be provided, saved, documented, etc., e.g., to a log file in procedure 218 after a light dosage has been applied to the nail. In some exemplary cases, the one or more parameters can be related to light dosage. For example, exemplary light dosage parameters can include start time of treatment, end time of treatment, treatment time (e.g., duration), the power of the light, and/or the light dosage. Recording, saving, storing and/or documenting information related to treatment (e.g., light dosage parameters) can facilitate a subsequent verification of light dosage by a review of the log file, any electronic file and/or any storage electronic facility which retains such information. In some exemplary cases, the log file may be reviewed by the user of the device or a medical professional. Alternatively, the log file, the electronic file and/or the storage electronic facility can be reviewed automatically (e.g., by a controller within the device) to ensure that over time (e.g., 1 week, 2 weeks, 3 weeks, 4 weeks, 5 weeks, etc.), an actual amount of delivered light dosage is compliant with a prescribed dosage and within a therapeutic range, as intended and/or desired according to the treatment plan. Ensuring that light dosage is delivered in a manner consistent with treatment is important, at least according to various exemplary embodiments of the present disclosure, at least because of a nature of dose response for photobiomodulation.

Figure 2B:
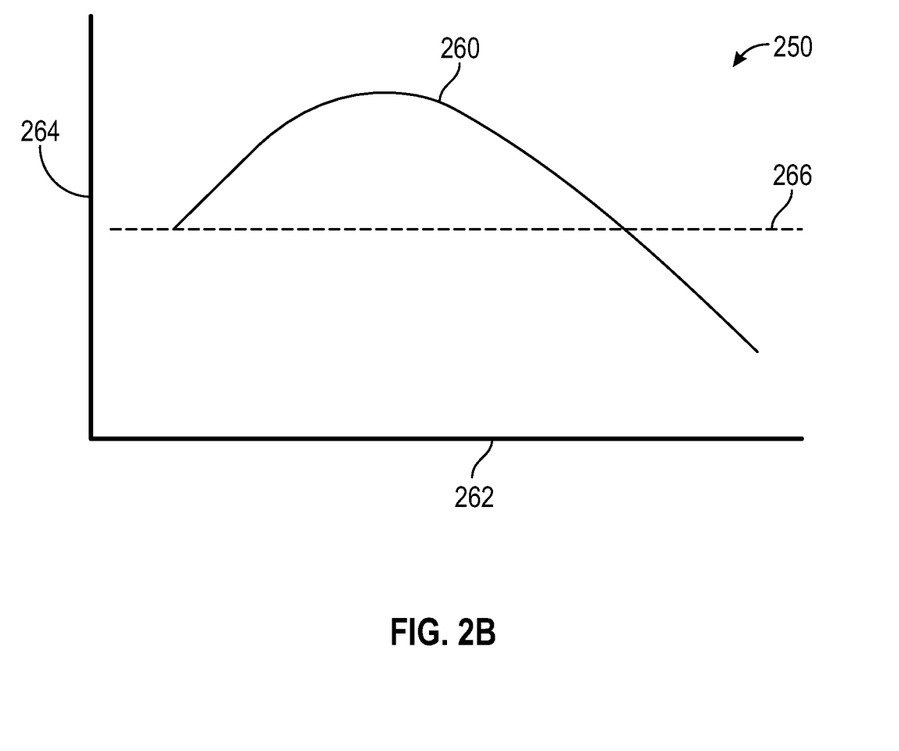
FIG. 2B is a graph providing an exemplary dose-response curve showing an Arndt-Schulz curve representing a biphasic dose response, in accordance with an exemplary embodiment of the present disclosure.

Photobiomodulation, which is at times referred to as low level light (or laser) therapy (LLLT), can act according to a biphasic (i.e., hormesis) dose-response relationship. Hormesis dose-responses can be understood as following the Arndt-Scholz rule of pharmacology: "*For every substance, small doses stimulate, moderate doses inhibit, and large doses kill.*" Thus, e.g., hormesis dose-response can be modeled using an Arndt-Schulz curve. FIG. 2B shows an exemplary dose-response graph 250 having an Arndt-Schulz curve 260 according to an exemplary embodiment of the present disclosure. A horizontal axis 262 indicates an exemplary dose, and a vertical axis 264 indicates an exemplary response. A dashed horizontal line 266 provides a control response indicating no dosage applied. For example, small dosages introduce an increasingly positive response, up to, e.g., a maximum at which increasing dosage reduces the response. Further increasing dosage can inhibit the exemplary response as the dose-response curve 260 falls below the control line 266. Huang, Sharma, Carroll, and Hamblin's 2011 publication entitled "Biphasic Dose Response in Low Level Light Therapy" published in Dose-Response, and incorporated herein by reference, describes research showing hormesis in LLLT dosage. The Huang publication enumerates 22 LLLT studies, including in vitro, animal, and clinical studies, which have shown hormesis. This publication demonstrates the difficulty biphasic (or even triphasic) dose responses can present for researchers as well as clinicians. As scientists and doctors are reporting on difficulties with the biphasic dosing of photobiomodultaion, such a device made available for use directly to a user, or in clinical or spa settings, should carefully control light dosage so as to prevent or at least reduce over-dosing and the possible resulting inhibitory effects.

Figure 3:
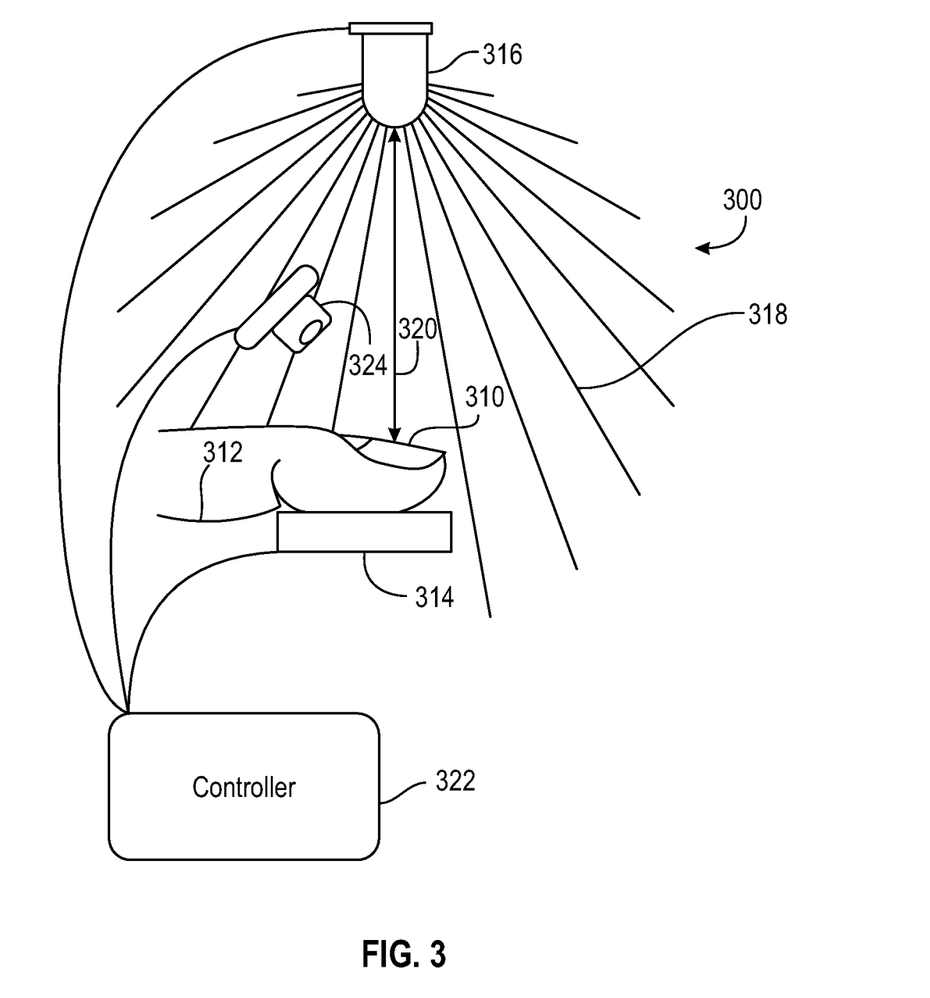
FIG. 3 is a diagram of a system for affecting nail growth, in accordance with an exemplary embodiment of the present disclosure.

FIG. 3 shows a diagram of a system 300 for treating a nail 310 to affect (e.g., increase) nail growth rate according to an exemplary embodiment of the present disclosure. As shown in FIG. 3, a nail 310 is attached to a limb 312 of the user. Limbs 312 include fingers, toes, and digits. It should be understood that limbs may also include legs, paws and any other anatomical structures that produce nails. For example, the limb 312 can be placed within an operational range of a presence detector 314. For example, in some exemplary embodiments, the presence detector can be a contact sensor which can comprise, e.g., a pressure sensor and/or a mechanical switch. In this exemplary case, the limb 312 contacts an element that is operationally coupled to the presence detector 314. In another exemplary embodiment, the presence detector can be a non-contact sensor. Examples of non-contact presence detectors can include Time-of-Flight (TOF) systems, LiDAR, capacitive proximity sensors, photoelectric sensors, optical sensors, and/or infrared sensors. A narrowband light source 316 can emit a narrowband light 318. The narrowband light 318 can have a nominal wavelength and a power. The narrowband light 318 irradiates the nail 310 at a treatment irradiance. According to some exemplary embodiments of the present disclosure, the treatment irradiance can be a function of the power of the narrowband light and/or a distance 320 between the narrowband light source 316 and the nail 310.

A controller 322 receives input (e.g., data, signals, etc.) from the presence detector 314, and can control the narrowband light source 316. The controller 322 can control the narrowband light source 316 in order to, e.g., accurately deliver a light dosage to the nail 310. In some exemplary embodiments, the light dosage can be controlled according to a treatment irradiance, typically measured in units of $W/cm^2$. Treatment irradiance is a function of the power of the light source 316 and/or the distance between the light source 316 and the nail 310. In some exemplary cases, output from the light source can be modeled according to Lambert's Sine Law; and, the light can be said to be Lambertian. In some exemplary variants and/or versions, the controller 322 can comprise a pulse width modulator (PWM) and/or similar electronic power regulator, to the power of the light 318 emitted by the narrowband light source 316. In some further exemplary embodiments, the light dosage can be measured in accumulated fluence, typically measured in units of $J/cm^2$. Accumulated fluence can be estimated by, e.g., integrating the treatment irradiance over a treatment time. Therefore, in some exemplary variants and/or versions, the controller 322 can control the light dosage by controlling the treatment time.

According to certain exemplary embodiments of the present disclosure, the controller 322 can control the light dosage based upon the treatment irradiance delivered to the nail 310. In some exemplary variants and/or versions, the controller 322 can additionally include an estimating system that can be configured to estimate the treatment irradiance. The estimating system—according to various exemplary embodiments of the present disclosure—can estimate the treatment irradiance based upon the presence of the nail 310, the distance 320 between the nail and the light source, and the power of the light 318. In some further exemplary variants and/or versions, the system 300 can also include a photodetector 324 that can be configured to measure the power of the light 318 and the treatment irradiance.

In the various exemplary variants and versions, the controller 322 can be configured to document, store, save and otherwise provide one or more treatment related parameters or variables electronically, e.g., to a log file, electronic storage file, etc. Such exemplary files—in some exemplary cases—can be located within a non-volatile memory located within the system 300, the controller 322, external storage device, etc. . . . . Exemplary non-volatile memories can include solid state drives (SSD), flash drives (e.g., NAND flash), hard drives (HDD), and read-only memory (ROM) (e.g., electrically erasable programmable ROM [EE-PROM]). In some cases, the exemplary files can be stored locally or remotely, and, e.g., the communication with such exemplary file(s) (e.g., reading, writing, analyzing, etc.) can be performed over one or more networks. Exemplary networks include local area networks (LAN), wide area networks (WAN), closed areas networks (CAN), and wireless networks (e.g., WiFi). In the exemplary cases where the exemplary file(s) is/are located remotely and accessed via one or more networks, the controller 322 can comprise a network interface (not shown). Exemplary network interfaces can include a network interface controller (NIC), a wireless network interface controller (WNIC), cellular network portable transceivers (e.g., 4g-LTE wireless broadband modem), a modem, and/or an integrated service digital network (ISDN) terminal adapter (TA). In some exemplary cases, such one or more parameters being documented, stored, saved, reviewed, analyzed, etc. e.g., in the exemplary file can include parameters related to light dosage, for example, a start time of treatment, an end time of treatment, the treatment time, the power of the light, and/or the light dosage. In certain exemplary embodiments of the present disclosure, the controller 322 can be further configured to review the exemplary (e.g., log, electronic, etc.) file to verify light dosage compliance to a treatment regimen. For example, in an exemplary case, the controller 322 can estimate a total light dosage delivered by the system 300 from the exemplary file over a given or predetermined time period (e.g., 1 day, 1 week, 2 weeks, etc.), and can be configured to determine if this light dosage is within limits of a prescribed or predetermined light dosage regimen.

Figure 4:
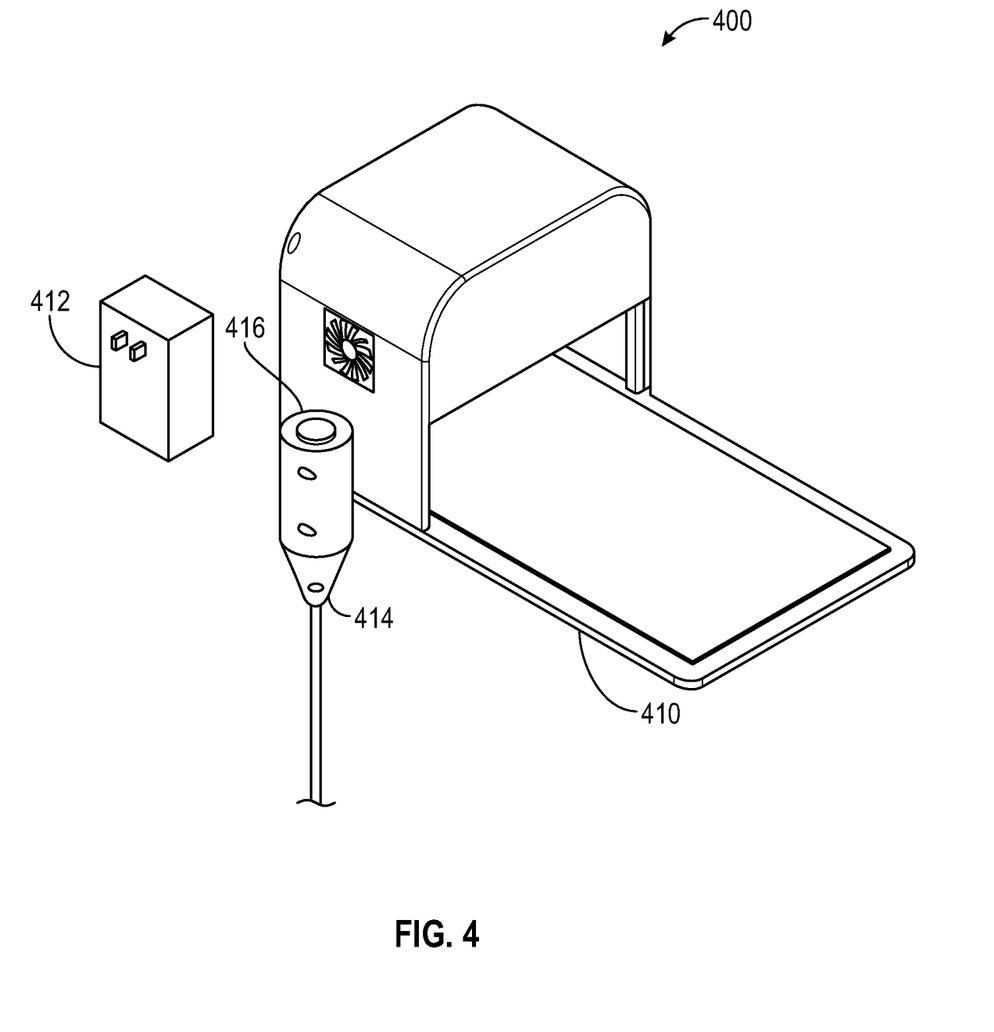
FIG. 4 is an illustration of the system for affecting nail growth, in accordance with another exemplary embodiment of the present disclosure.

A diagram of a system 400 for treatment of nails according to another exemplary embodiment of the present disclosure is shown in FIG. 4. The exemplary system 400 can include a base 410 into which a limb (e.g. foot or hand) can be placed. The exemplary base 410 can be powered by a power supply 412 that can be connected to a wall outlet and/or by any other power providing device (including batteries or a standalone power device). The base 410 can be operated using a remote interface 414. The remote interface 414 can be used to initiate, maintain, modify and/or stop treatment. The remote interface 414 can additionally comprise an indicator light 416 (or any other visual and/or audio indicator) that can indicate the status of the system 400. In one example, the indicator light 416 can show an orange light the system 400 is ready to treat after having detected a presence of a nail; a green light during treatment; and a red light for post-treatment.

Figure 5:
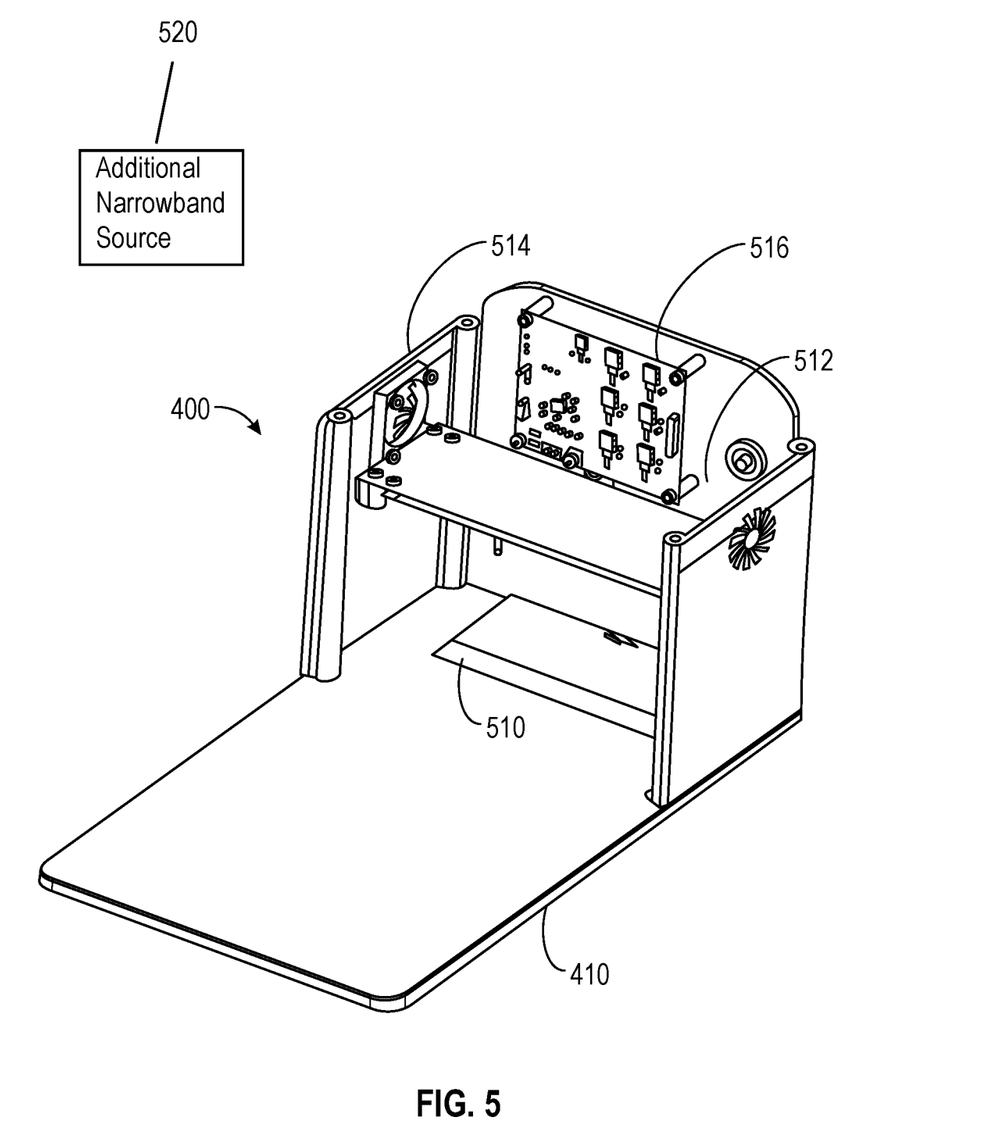
FIG. 5 is a perspective disassembled view of the system for affecting nail growth, shown in FIG. 4.

The exemplary system 400 is shown without a cover in FIG. 5, in accordance with the exemplary embodiments of the present disclosure. A presence detector 510 is provided at the bottom of the base 510, although the location thereof can include a side, tom$_{[41]}$ and any other locations on or near the base 510. A nonlimiting example of such exemplary presence detector 510 can be the capacitive sensor built into the microcontroller (MCU) TI MSP430FR2633 available at http.//www.ti.com/product/MSP430FR2633. Above the exemplary presence detector 510, it is possible to provide a light emitting diode (LED) board 512, although any other location within the vicinity of the base 510 is possible and within the scope of the present disclosure. The LED board 512 can emit the narrowband light using an array of LEDs (e.g., narrowband light sources). Nonlimiting examples of such exemplary LED arrays can include, among others, Luxeon Z Color Line (Lumileds)—660 nm available at https://www.luxeonstar.com./asstes/downloads/ds105.pdf and Luxeon IR Compact Line (Lumileds)-850 nm available at https://www.luxeonstar.com./asstes/downloads/ds190.pdf. According to certain exemplary embodiments of the present disclosure, the array of LEDs can be configured to emit narrowband light at one or more wavelengths (e.g., 850 nm and 665 nm). In further exemplary embodiments of the present disclosure, the LED board 512 is actively cooled by a fan 514. Finally, a controller 516 is shown that controls the LED board 512 based, at least partially, on feedback provided by the presence detector 510 and/or the remote interface 414.

Figure 6:
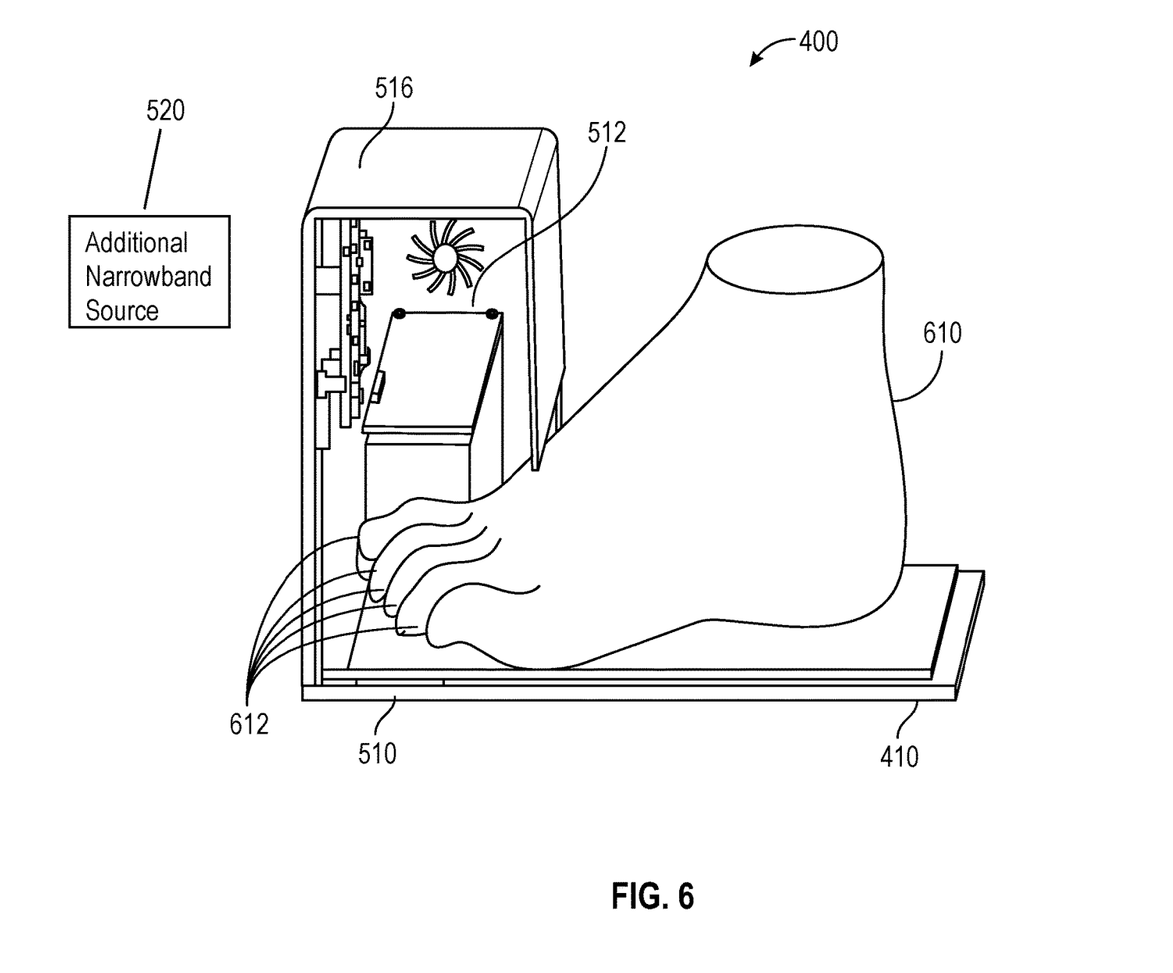
FIG. 6 is an illustration of a system being used for affecting toenail growth, in accordance with yet another exemplary embodiment of the present disclosure.
Figure 7:
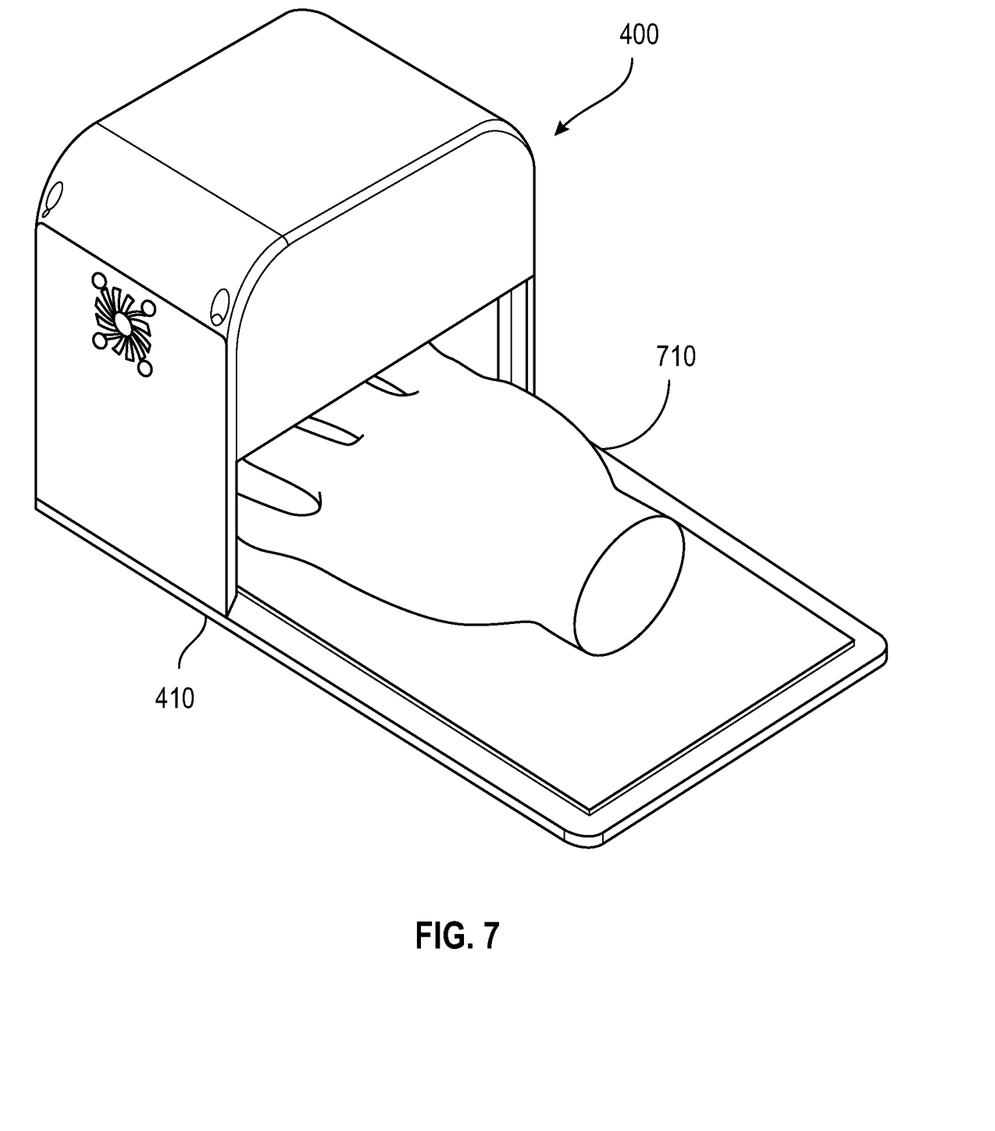
FIG. 7 is an illustration of a system being used for affecting fingernail growth, in accordance with still another exemplary embodiment of the present disclosure; and, FIG. 8 is a graph illustrating exemplary results from a study, in accordance with an exemplary embodiment of the present disclosure.

FIG. 6 shows a cross-sectional view of an illustration of an exemplary treatment of toenails using the exemplary system 400, in accordance with an exemplary embodiment of the present disclosure. For example, a foot 610 can be placed inside the base 410. The presences of the foot 610 and toes can detected by the presence detector 510. The LED board 512 can be positioned a known/predetermined distance from one or more toenails 612 belonging to the foot 610. Treatment can be initiated by the remote interface 414, and one or more narrowband lights can be emitted from the LED board 512 and can be incident the one or more toenails 612. The controller 516 can control a dosage of narrowband light, for example, by controlling a power and on-time of the LED array. FIG. 7 shows a hand 710 placed inside the base 410 of the exemplary system 400 for treating one or more fingernails (not shown), in accordance with an exemplary embodiment of the present disclosure.

As described in detail herein above, wavelength selection and light dosage can determine changes in nail growth rate. The biphasic dose-response for photobiomodulation facilitates stimulating effects or inhibitory effects to be realized by varying dose. An optimum stimulating light dosage can be sought and/or obtained for the exemplary embodiments of the present disclosure which are configured to increase nail growth rate. For example, in one exemplary embodiment, a maximum inhibiting light dosage can be sought for the exemplary embodiments configured to suppress nail growth rate. A limiting characteristic for the maximum inhibiting light dosage can be typically heat. Increasing treatment irradiance can ultimately heat the nail bed and limb resulting in discomfort and in extreme cases, thermal disruption.

A table below enumerates exemplary narrowband wavelengths for nail treatment according to certain exemplary embodiments of the present disclosure:

| Representative Treatment Wavelength (nm) | Wavelength Range (nm) | List of Narrowband Light Nom. Center Wavelengths (nm) |
|---|---|---|
| 665 | 600-700 | 600, 610, 620, 635, 640, 643, 650, 660, and 680 |
| 765 | 700-800 | 720, 730, 740, 765, and 770 |
| 850 | 800-900 | 810, 820, 830, 850, 855, 856, 870, 875, 880, 885, 890, and 900 |

A table below enumerates exemplary light dosages, according to certain exemplary embodiments of the present disclosure:

| Nom. Wavelength (nm) | Min. Irradiance (W/cm$^2$) | Nom. Irradiance (W/cm$^2$) | Max. Irradiance (W/cm$^2$) | Min. Fluence (J/cm$^2$) | Nom. Fluence (J/cm$^2$) | Max. Fluence (J/cm$^2$) | Min. Time (S) | Nom. Time (S) | Max. Time (S) |
|---|---|---|---|---|---|---|---|---|---|
| 665 | 0.0005 | 0.008 | 5 | 0.5 | 5 | 50 | 60 | 600 | 14400 |
| 765 | 0.0005 | 0.008 | 10 | 0.5 | 5 | 100 | 60 | 600 | 14400 |
| 850 | 0.001 | 0.008 | 10 | 1 | 5 | 100 | 60 | 600 | 14400 |

It can certainly be appreciated that, for example, additional exemplary embodiments can be provided that can include wavelengths not described in detail above, including, e.g.: 265-275 nm, 275 nm, 278 nm, 280 nm, 285 nm, 295 nm, 310 nm, 325 nm, 340 nm, 355 nm, 357 nm, 365 nm, 365-375 nm, 367 nm, 368 nm, 370 nm, 375 nm, 377 nm, 378 nm, 380 nm, 370-385 nm, 380-390 nm, 382 nm, 383 nm, 385 nm, 388 nm, 390 nm, 395 nm, 400 nm, 402 nm, 403 nm, 405 nm, 410 nm, 415 nm, 420 nm, 425 nm, 430 nm, 447 nm, 450 nm, 460 nm, 470 nm, 502 nm, 520 nm, 525 nm, 527 nm, 562 nm, 570 nm, 590 nm, 595 nm, 597 nm, 905 nm, 920 nm, 935 nm, 940 nm, 945 nm, 950 nm, 980 nm, 1020 nm, 4050 nm, 4060 nm, 1200 nm, 1300 nm, 1450 nm, 1550 nm, 1650 nm, and 1720 nm.

In another additional exemplary embodiment for treatment of onychomycosis, an additional narrowband light source 520 can emit a supplementary narrowband light (see, e.g., FIGS. 5 and 6). The supplementary light can have a wavelength and dosage selected to damage fungal mycelium. For example, a near IR wavelength (700 nm-2000 nm) having a relatively large dose can be used to heat the nail plate to a temperature that will disrupt the mycelium. In another exemplary variant and/or version, a UV wavelength (e.g., 200 nm-400 nm) having a smaller light dosage can be employed to disrupt the mycelium through photonic (e.g., non-thermal) configurations/ways.

In another additional exemplary embodiment of the present disclosure, the biphasic light dose response can be used to intentionally produce an inhibitory response in nail growth rate. In such exemplary case, a light dosage controlled above a threshold at which inhibitory effects result.

In another a further exemplary embodiment of the present disclosure, treatment and light dosage can be controlled according to a dosing schedule. The dosing schedule is prescribed to induce a desired effect on the nail growth rate. For example, the dosing schedule in certain exemplary versions facilitates a user to be treated only once a day for a certain number of hours, days, etc. The dosing schedule can be controlled by the controller and can prevent and/or modify operation of the device at times outside the schedule, for example to prevent or reduce overdosage. In other exemplary variants and/or versions, the dosing schedule can be provided as regiment for treatment (e.g., directions for use) and the user is responsible for facilitating treatment according to the dosing schedule. Exemplary dosing schedules can include a frequency (e.g., four times a day, three times a day, twice a day, once a day, once every two days, once every three days, once every four days, etc.) and a duration (e.g., within a range of ten seconds to two hours).

In some exemplary cases, an electronic (e.g., log) file can be maintained in which parameters or variables related to light dosage are documented, stored, analyzed, recorded, etc. Actual light dosages delivered, according to the electronic file, may then be compared with the prescribed light dosage schedule in order to ensure that a proper amount of light is being delivered. As described above, in many exemplary cases, precise delivery of a light dosage can result in a desired nail growth change, where a little higher dosage (or a little lower dosage) can result in no or little change in nail growth or even a change in nail growth rate that is the opposite of the desired nail growth change (e.g., decreasing nail growth rate instead of increasing nail growth rate).

The exemplary device 400 described herein and shown in FIGS. 4-7 was used in a clinical trial to test efficacy of treatment on toenails. Fourteen subjects were enrolled in and successfully completed the trial. After a baseline toenail growth rate was established, treatment using the device 400 was performed daily for 6 weeks. Treatment light dosage used during the trial is described in a table below:

| | |
|---|---|
| Wavelength of light | 660 nm and 850 nm |
| Delivered light dosage range | Within a range of 2.1 J/cm$^2$ and 16 J/cm$^2$ |
| Exposure time | 10 minutes |
| Maximum light intensity | No greater than 30 mW/cm$^2$ |

The treatment was self-administered by the subjects. Nail growth rate was determined by examining photographs of the treated toenails. The toenails were marked and the mark was used in the photographs to gauge growth.

Figure 8:
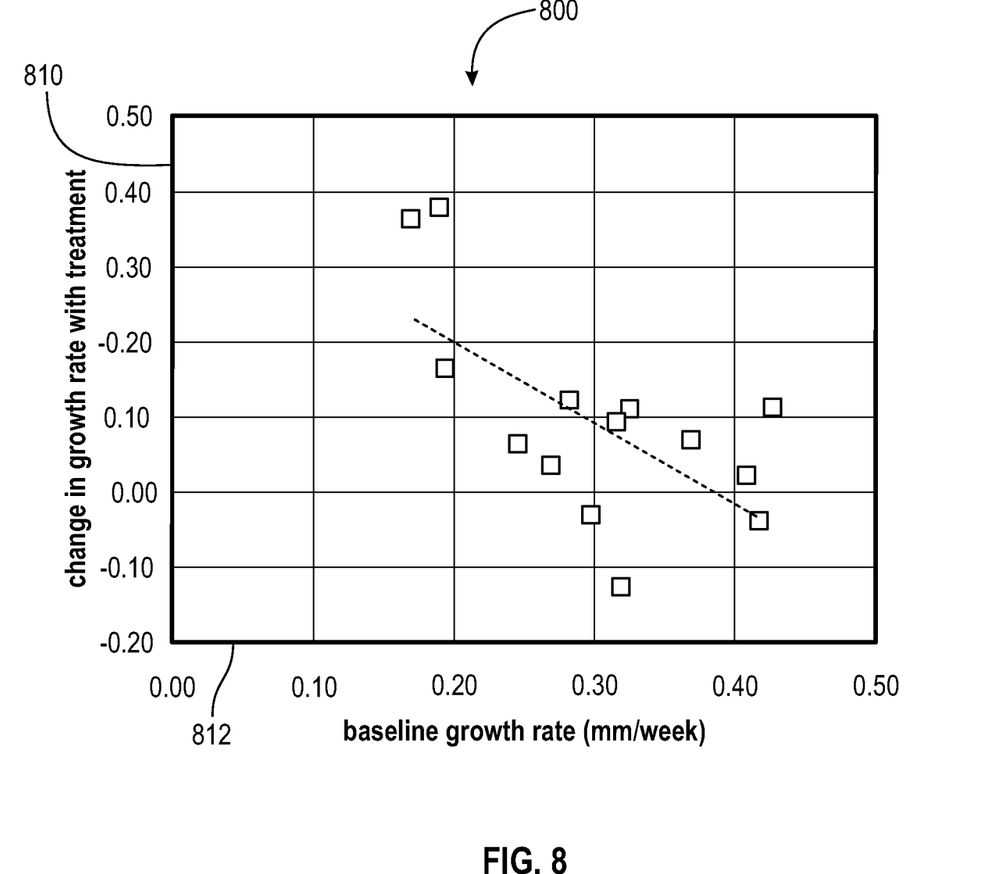

FIG. 8 shows a graph 800 that illustrates a relative change in toenail growth in percentage along a vertical axis 810 against a baseline growth in millimeters per week along a horizontal axis 820. As shown in FIG. 8 that those subjects having the lowest baseline growth rate (e.g., less than 0.20 mm/week) appear to experience the largest increase in relative growth rate change (up to 40%). It is therefore demonstrated that the treatment appears to positively affect slow growing toenails.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

What is claimed is:

1. A method for affecting a growth rate of a nail of a digit of a subject, comprising:
   detecting, using a presence detector, a presence of the nail or the digit;
   irradiating, using a narrowband light source, the nail over a treatment time using a light;
   controlling, using a controller, at least one of (a) a power of the light or (b) the treatment time to irradiate the nail with a dosage of the light that is within a biphasic light dosage range, wherein a wavelength of the light and the dosage of the light are (i) configured to affect a growth rate of the nail, and (ii) provided in a range of 502 nm-980 nm; and
   recording, using the controller, at least one parameter related to the dosage of the light as electronic information.

2. The method of claim 1, wherein the wavelength of the light is at least one of 658 nm, 665 nm, 765 nm, 850 nm, or 855 nm.

3. The method of claim 2, wherein the biphasic light dosage range is bounded by (a) a lesser light dosage which is about 0.5 J/cm$^2$, and (b) a greater light dosage that is about 100 J/cm$^2$.

4. The method of claim 3, wherein the treatment time is between 60 seconds and 14400 seconds.

5. The method of claim 1, further comprising:
estimating or determining a treatment irradiance for the nail based on (a) the presence of the nail or the digit at a known location, and (b) a power of the light; and
controlling the dosage of the light based on the treatment irradiance.

6. The method of claim 1, further comprising:
measuring, using a photodetector, a treatment irradiance for the nail; and
controlling the dosage of the light based on the treatment irradiance.

7. The method of claim 1, wherein the narrowband light source comprises at least one of a light emitting diode, a light emitting capacitor, a laser, a flash lamp, or a filtered wideband light source.

8. The method of claim 1, wherein the method is configured to increase the growth rate of the nail or decrease the growth rate of the nail.

9. The method of claim 1, wherein the at least one parameter related to the dosage of the light comprises at least one of a start time of treatment, an end time of treatment, the power of the light, the treatment time of the light, or the dosage of the light.

10. The method of claim 9, further comprising verifying the dosage of the light for compliance using the electronic information.

11. The method of claim 1, further comprising controlling, using the controller, the dosage of the light based upon a dosing schedule.

12. The method of claim 1, wherein the presence detector comprises at least one of a pressure sensor, a camera, a time of flight (TOF) system, a LiDAR system, a capacitive proximity sensor, a photoelectric sensor, an optical sensor, an infrared sensors, or a switch.

13. The method of claim 1, wherein the wavelength of the light and the dosage of the light is provided in a range of 600 nm-850 nm.

14. The method of claim 1, further comprising:
irradiating, using a further narrowband light source, the nail over using a further light; and
controlling, using the controller, at least one of (a) a power of the further light or (b) the treatment time to irradiate the nail with a further dosage of the further light.

15. The method of claim 14, wherein a further wavelength of the further light and a further dosage of the further light are provided in a range of 700 nm-2000 nm.

16. The method of claim 14, wherein a further wavelength of the further light and a further dosage of the further light are provided in a range of 700 nm-2000 nm.

17. A system for affecting a growth rate of a nail of a digit of a subject, the system comprising:
a presence detector configured to detect a presence of the nail or the digit;
a narrowband light source configured to irradiate the nail over a treatment time using a light; and
a controller configured to control at least one of (a) a power of the light or (b) the treatment time to irradiate the nail with a dosage of the light that is within a biphasic light dosage range, wherein a wavelength of the light and the dosage of the light are (ii) configured to affect a growth rate of the nail and (ii) provided in a range of 502 nm-980 nm, and wherein the controller is configured to record at least one parameter related to the dosage of the light as electronic information.

18. The system of claim 17, wherein the wavelength of the light is at least one of 658 nm, 665 nm, 765 nm, 850 nm, or 855 nm.

19. The system of claim 18, wherein the biphasic light dosage range is bounded by (a) a lesser light dosage which is about 0.5 J/cm$^2$, and (b) a greater light dosage that is about 100 J/cm$^2$.

20. The system of claim 19, wherein the treatment time is between 60 seconds and 14400 seconds.

21. The system of claim 18, wherein the at least one parameter related to the dosage of the light comprises at least one of a start time of treatment, an end time of treatment, the power of the light, the treatment time of the light, or the dosage of the light.

22. The system of claim 21, wherein the controller is configured to verify the dosage of the light for compliance using the electronic information.

23. The system of claim 17, wherein the controller is configured to:
estimate or determining a treatment irradiance for the nail based on (a) the presence of the nail or the digit at a known location, and (b) a power of the light; and
control the dosage of the light based on the treatment irradiance.

24. The system of claim 17, comprising:
a photodetector configured to measure a treatment irradiance for the nail; and
wherein the controller is configured to control the dosage of the light based on the treatment irradiance.

25. The system of claim 17, wherein the narrowband light source comprises at least one of a light emitting diode, a light emitting capacitor, a laser, a flash lamp, or a filtered wideband light source.

26. The system of claim 17, wherein the system is configured to increase the growth rate of the nail or decrease the growth rate of the nail.

27. The system of claim 17, wherein the controller is configured to control the dosage of the light based on a dosing schedule.

28. The system of claim 17, wherein the presence detector comprises at least one of a pressure sensor, a camera, a time of flight (TOF) system, a LiDAR system, a capacitive proximity sensor, a photoelectric sensor, an optical sensor, an infrared sensors, or a switch.

29. The system of claim 17, wherein the wavelength of the light and the dosage of the light is provided in a range of 600 nm-850 nm.

30. The system of claim 17, further comprising:
a further narrowband light source irradiating the nail over using a further light, wherein the controller is further configured to control at least one of (a) a power of the further light or (b) the treatment time to irradiate the nail with a further dosage of the further light.

* * * * *